(12) United States Patent
Masoud et al.

(10) Patent No.: US 8,868,794 B2
(45) Date of Patent: Oct. 21, 2014

(54) APPLICATION LIMITATIONS FOR A MEDICAL COMMUNICATION MODULE AND HOST DEVICE

(75) Inventors: Javaid Masoud, Shoreview, MN (US); William D. Verhoef, Andover, MN (US); Gregory J. Haubrich, Champlin, MN (US); Christopher M. Petersen, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 177 days.

(21) Appl. No.: 13/336,464

(22) Filed: Dec. 23, 2011

(65) Prior Publication Data

US 2012/0166680 A1    Jun. 28, 2012

Related U.S. Application Data

(60) Provisional application No. 61/427,390, filed on Dec. 27, 2010.

(51) Int. Cl.
| | | |
|---|---|---|
| *G06F 3/00* | (2006.01) | |
| *A61B 5/00* | (2006.01) | |
| *A61N 1/372* | (2006.01) | |
| *G06F 19/00* | (2011.01) | |

(52) U.S. Cl.
  CPC .......... *A61N 1/37235* (2013.01); *A61B 5/0024* (2013.01); *A61B 2560/0276* (2013.01); *A61N 1/37252* (2013.01); *G06F 19/3468* (2013.01); *A61B 5/6898* (2013.01); *G06F 19/3418* (2013.01); *G06F 19/3406* (2013.01); *G06F 19/3481* (2013.01); *G06F 19/3475* (2013.01); *A61B 5/0022* (2013.01)
  USPC .......................................................... 710/5

(58) Field of Classification Search
  None
  See application file for complete search history.

(56) References Cited

U.S. PATENT DOCUMENTS

| | | |
|---|---|---|
| 5,720,770 A | 2/1998 | Nappholz et al. |
| 5,748,103 A | 5/1998 | Flach et al. |

(Continued)

FOREIGN PATENT DOCUMENTS

| | | |
|---|---|---|
| KR | 2010/0005967 | 6/2010 |
| WO | WO 01/33796 A1 | 5/2001 |

(Continued)

OTHER PUBLICATIONS (PCT/US2011/067177) PCT Notification of Transmittal of the International Search Report and the Written Opinion of the International Searching Authority, 12 pages.

(Continued)

*Primary Examiner* — Idriss N Alrobaye
*Assistant Examiner* — Richard B Franklin
(74) *Attorney, Agent, or Firm* — Michael J. Ostrom; Stephen W. Bauer

(57) ABSTRACT

System and method for interfacing with a medical device having a host device and a communication module. The host device has a user interface configured to input and display information relating to the interfacing with the medical device. The communication module is locally coupled to the host device and configured to communicate wirelessly with the medical device. The system, implemented by the host device and the communication module, is configured to communicate with the medical device with functions. The system, implemented by at least one of the host device and the communication module, has a security condition. At least one of the functions is disabled, at least in part, from operating on the system based upon the security condition.

20 Claims, 9 Drawing Sheets

(56) References Cited

U.S. PATENT DOCUMENTS

| | | |
|---|---|---|
| 5,748,104 A | 5/1998 | Argyroudis et al. |
| 5,772,586 A | 6/1998 | Heinonen et al. |
| 6,442,432 B2 | 8/2002 | Lee |
| 6,556,630 B1 | 4/2003 | Brinsfield et al. |
| 6,561,975 B1 | 5/2003 | Pool et al. |
| 6,577,901 B2 | 6/2003 | Thompson |
| 6,708,065 B2 | 3/2004 | Von Arx et al. |
| 6,749,566 B2 | 6/2004 | Russ |
| 6,757,523 B2 | 6/2004 | Fry |
| 6,804,558 B2 | 10/2004 | Haller et al. |
| 6,805,667 B2 | 10/2004 | Christopherson et al. |
| 6,840,904 B2 | 1/2005 | Goldberg |
| 6,959,182 B2 | 10/2005 | Lingafeldt et al. |
| 6,985,088 B2 | 1/2006 | Goetz et al. |
| 7,096,068 B2 | 8/2006 | Mass et al. |
| 7,156,809 B2 | 1/2007 | Quy |
| 7,174,216 B1 | 2/2007 | Dalal |
| 7,181,505 B2 | 2/2007 | Haller et al. |
| 7,256,695 B2 | 8/2007 | Hamel et al. |
| 7,289,855 B2 | 10/2007 | Nghiem et al. |
| 7,292,828 B1 | 11/2007 | Liu et al. |
| 7,294,105 B1 | 11/2007 | Islam |
| 7,330,763 B1 | 2/2008 | Cullen et al. |
| 7,408,898 B1 | 8/2008 | Brown |
| 7,466,235 B1 | 12/2008 | Kolb et al. |
| 7,656,673 B1 | 2/2010 | Fries et al. |
| 8,265,556 B2 | 9/2012 | Tekin et al. |
| 2002/0019749 A1 | 2/2002 | Becker et al. |
| 2002/0052539 A1 | 5/2002 | Haller et al. |
| 2003/0144711 A1* | 7/2003 | Pless et al. ............... 607/60 |
| 2003/0206192 A1 | 11/2003 | Chen et al. |
| 2004/0077347 A1 | 4/2004 | Lauber et al. |
| 2004/0088020 A1 | 5/2004 | Condie et al. |
| 2004/0090950 A1 | 5/2004 | Lauber et al. |
| 2004/0122488 A1 | 6/2004 | Mazar et al. |
| 2005/0061336 A1 | 3/2005 | Goetz et al. |
| 2005/0071199 A1 | 3/2005 | Riff |
| 2005/0080652 A1 | 4/2005 | Brown |
| 2006/0075174 A1 | 4/2006 | Vuong |
| 2006/0089543 A1 | 4/2006 | Kim et al. |
| 2006/0111759 A1* | 5/2006 | Hoyme et al. ............ 607/60 |
| 2006/0189854 A1 | 8/2006 | Webb et al. |
| 2006/0190051 A1 | 8/2006 | Gerber et al. |
| 2006/0202805 A1 | 9/2006 | Schulman et al. |
| 2006/0220901 A1* | 10/2006 | Ginggen et al. ...... 340/825.69 |
| 2006/0247710 A1 | 11/2006 | Goetz et al. |
| 2007/0015973 A1 | 1/2007 | Nanikashvili |
| 2007/0094657 A1 | 4/2007 | Jayasinghe |
| 2007/0106129 A1 | 5/2007 | Srivahsa et al. |
| 2007/0123955 A1 | 5/2007 | Verhoef et al. |
| 2007/0213657 A1 | 9/2007 | Jennewine et al. |
| 2007/0226260 A1 | 9/2007 | Williams et al. |
| 2007/0233206 A1 | 10/2007 | Frikart et al. |
| 2007/0238936 A1 | 10/2007 | Becker |
| 2007/0251835 A1 | 11/2007 | Mehta et al. |
| 2008/0070599 A1 | 3/2008 | Apodaca et al. |
| 2008/0077431 A1 | 3/2008 | Calder et al. |
| 2008/0082144 A1 | 4/2008 | Marcotte et al. |
| 2008/0119705 A1 | 5/2008 | Patel et al. |
| 2008/0126653 A1 | 5/2008 | King et al. |
| 2008/0140163 A1 | 6/2008 | Keacher et al. |
| 2008/0146890 A1 | 6/2008 | LeBoeuf et al. |
| 2008/0183245 A1 | 7/2008 | Van Oort et al. |
| 2008/0214903 A1 | 9/2008 | Orbach |
| 2008/0249387 A1 | 10/2008 | Hogan |
| 2009/0006419 A1 | 1/2009 | Savitsky et al. |
| 2009/0055322 A1 | 2/2009 | Bykov et al. |
| 2009/0058635 A1 | 3/2009 | LaLonde et al. |
| 2009/0062623 A1 | 3/2009 | Cohen et al. |
| 2009/0083070 A1 | 3/2009 | Giftakis et al. |
| 2009/0105787 A1 | 4/2009 | Kokones et al. |
| 2009/0164253 A1 | 6/2009 | Lyshkow |
| 2009/0182206 A1 | 7/2009 | Najafi et al. |
| 2009/0229610 A1 | 9/2009 | Oates et al. |
| 2009/0240120 A1 | 9/2009 | Mensinger et al. |
| 2009/0326356 A1 | 12/2009 | Kracker |
| 2009/0326981 A1 | 12/2009 | Karkanias et al. |
| 2010/0016700 A1 | 1/2010 | Sieh et al. |
| 2010/0081411 A1 | 4/2010 | Montenero |
| 2010/0085418 A1 | 4/2010 | Sampsel et al. |
| 2010/0259543 A1 | 10/2010 | Tarassenko et al. |
| 2010/0292556 A1 | 11/2010 | Golden |

FOREIGN PATENT DOCUMENTS

| | | |
|---|---|---|
| WO | 03/077993 A1 | 9/2003 |
| WO | WO 2008/034898 A1 | 3/2008 |
| WO | WO 2009/046214 A1 | 4/2009 |
| WO | WO 2009/055608 A2 | 4/2009 |
| WO | WO 2009/134478 A1 | 11/2009 |
| WO | 2010/132617 A2 | 11/2010 |

OTHER PUBLICATIONS http://www.webservusb.com/.
http://www.pendriveapps.com/usb-webserver/.
"USB Webserver—Portable Web Server"; http://www.pendriveapps.com/usb-webserver; 5 pages; Retrieved Jan. 18, 2011.
"WebServ USB"; http://web.archive.org/web/20040805050711/http://www.webservusb.com; 2 pages; Retrieved Jan. 18, 2011.

* cited by examiner

APPLICATION LIMITATIONS FOR A MEDICAL COMMUNICATION MODULE AND HOST DEVICE

RELATED APPLICATION

This application claims priority from U.S. Provisional Application No. 61/427,390, filed on Dec. 27, 2010, entitled "APPLICATION LIMITATIONS FOR A MEDICAL COMMUNICATION MODULE AND HOST DEVICE".

FIELD

The present invention related generally to medical communication devices and, more particularly, to devices to communicate with a medical device.

BACKGROUND

Commercial consumer electronic devices or other so-called "off-the-shelf" electronic devices for providing computing operations and communications, both wired and wireless, are well known in the art. Devices such as personal digital assistants ("PDAs"), "smartphones" and tablet personal computers provide computing power, digital storage and user input/output functionality in what is, typically, a size and weight which is conducive to easy portability by an individual user. In addition, so-called "netbooks", as well as notebook and laptop computers, may provide similar functionality, albeit commonly in a larger form-factor and with greater weight.

Commonly, such devices listed above incorporate a communications module or communications modules to allow the devices to communicate over various wireless communications bands. Standards such as Bluetooth, IEEE 802.11, cellular, among others known in the art, provide both protocols and designated frequencies over which communications may occur. In addition, proprietary communications schemes may be developed and fielded independently. Communications modules designed to be consistent with such commercial and proprietary standards may be incorporated into such devices to permit them to communicate wirelessly with other devices similarly designed to communicate according to the various standards.

Electrically active medical devices may similarly be configured to communicate according to commercial and proprietary communication standards. Such medical devices may be involved in communications to transmit data relating to the condition of the medical device as well as the condition of the patient with which the device is associated. In addition, the medical device may be involved with communications to receive commands from external sources pertaining to the function of the medical device, for instance to reprogram the medical device from a first configuration setting to a second configuration setting. The Medical Implant Communication Service ("MICS") band is commonly used to communicate with an implanted medical device. The Medical Data Service ("MEDS") is an ultra-low power medical device communication system using the 401-402 megaHertz and/or 405-406 megaHertz bands.

But while medical devices may, like commercial devices, operate according to various communication standards, the standards according to which the medical devices operate may not advantageously be the same as those to which commercial devices operate. While a commercial device may usefully communicate according to, for instance, the Bluetooth communication standard, the power requirements of Bluetooth may make using Bluetooth disadvantageous for an implantable medical device incorporating a relatively small power source. Such an implantable medical device may advantageously utilize a proprietary communication scheme over the MICS/MEDS band instead. By contrast, a smartphone, for instance, which does not commonly communicate with implantable medical devices, and which, as such, may not profitably incorporate a MICS/MEDS band receiver, may not be able to communicate with an implantable medical device.

As a result, communications with implantable medical devices have commonly incorporated proprietary, custom-designed electronic devices instead of commercial, off-the-shelf devices. Custom designed electronic devices tend to cost relatively more for design and manufacture of relatively small numbers of proprietary devices in comparison with the number of commercial devices on the market. Because of the increased cost, there may be a motivation to minimize the number of such custom-designed devices built to a relative minimum in order to save cost. This may tend to limit availability of such custom-designed electronics, reducing a utility in providing the capabilities afforded by such electronics to users other than medical professionals in a clinical setting.

SUMMARY

It has been determined, however, that the relative proliferation of commercial devices such as smartphones, tablet computers, notebook computers and netbooks may provide an opportunity to adapt such devices with custom-designed modules to be used with existing or future commercial devices for communication with medical devices. By virtue of not being complete user-operable devices, such proprietary modules may be relatively inexpensive to manufacture and distribute. By adapting the performance of commercial devices with proprietary modules, the utility which may be provided with proprietary modules may be made available to a wide range of users beyond medical professionals in clinical settings, such as to the patients themselves or other healthcare providers, while remaining relatively cost effective.

By providing patients and others an ability to communicate between commercial devices and medical devices, patients, medical professionals and medical devices may obtain greater exposure to information which may benefit the treatment of the patient. By providing modules to adapt commercial electronic devices for use interfacing with and presenting information from implantable medical devices and conducting interviews and follow-ups between patients and physicians, relatively greater information and ability to interact between and among various devices and entities may be available than has been available in the past. Such information and interaction may further be made available at relatively reduced cost to health care systems than has previously been possible or realistic.

Device applications may be utilized an impact performance in such circumstances. Programs which run on the commercial device may or may not have relevance to utilizing or interfacing with the medical device. To the extent that such applications are useful, they may be managed to reduce a likelihood of being improperly utilized. To the extent that such applications are not useful, they may be managed to reduce a likelihood of interference with applications which are relevant to utilizing or interfacing with the medical device.

In an embodiment, a system for interfacing with a medical device comprises a host device and a communication module. The host device comprises a user interface configured to input and display information relating to the interfacing with the medical device. The communication module is locally coupled to the host device and configured to communicate wirelessly with the medical device. The system, implemented by the host device and the communication module, is configured to communicate with the medical device with a plurality of functions. The system, implemented by at least one of the host device and the communication module, has a security condition. At least one of the plurality of functions is disabled, at least in part, from operating on the system based upon the security condition.

In an embodiment, at least one of the plurality of functions operates on the system by running an application on at least one of the host device and the communication module and wherein the at least one of the plurality of functions is disabled by at least partially deleting the application.

In an embodiment, at least one of the plurality of functions is disabled by deleting the application.

In an embodiment, the application implements the at least one of the plurality of functions by running the application on the host device.

In an embodiment, the application is disabled by removing the application from the host device.

In an embodiment, the application is disabled by moving the application from the host device to the communication module.

In an embodiment, the at least one of the plurality of functions disabled based upon the security condition is a communication function with the medical device.

In an embodiment, the at least one of the plurality of functions deleted is configured to be restored to the system only by a trusted source.

In an embodiment, a system for interfacing with a medical device comprises a host device and a communication module. The host device comprises a user interface configured to input and display information relating to the interfacing with the medical device. The communication module is locally coupled to the host device and configured to communicate wirelessly with the medical device. The system, implemented by the host device and the communication module, is configured to communicate with the medical device with a function. The system is further configured so that the function operates, at least in part, only for a predetermined duration.

In an embodiment, the predetermined duration comprises a duration of operation of the function.

In an embodiment, the predetermined duration comprises a duration of elapsed time.

In an embodiment, the predetermined duration comprises a combination based, at least in part, on both a duration of operation of the function and a duration of elapsed time.

In an embodiment, the function is characterized by a number of operations and wherein the predetermined duration comprises a duration based, at least in part, on the number of operations.

In an embodiment, the function is characterized by a number of operations and wherein the predetermined duration comprises a duration based, at least in part, on a combination of the number of operations and a duration of elapsed time.

In an embodiment, the function is characterized by a number of operations and wherein the predetermined duration comprises a duration based, at least in part, on a combination of the number of operations and a duration of operation of the function.

In an embodiment, the function is characterized by a number of operations and wherein the predetermined duration comprises a duration based, at least in part, on a combination of the number of operations, a duration of operation of the function and a duration of elapsed time.

In an embodiment, the predetermined duration commences upon a first operation of the function.

In an embodiment, the predetermined duration commences upon an installation of the function on the system.

In an embodiment, the predetermined duration is extendable upon a user input.

In an embodiment, the user input is from a trusted source.

In an embodiment, a system for interfacing with a medical device comprises a host device and a communication module. The host device comprises a user interface configured to input and display information relating to the interfacing with the medical device. The communication module is locally coupled to the host device and is configured to communicate wirelessly with the medical device. The system, implemented by the host device and the communication module, is configured to communicate with the medical device with a plurality of functions. The system, implemented by at least one of the host device and the communication module, has a security condition. A first one of the plurality of functions is related to the interfacing with the medical device and a second one of the plurality of functions is not related with the interfacing with the medical device, wherein an operation of the second one of the plurality of functions is limited based, at least in part, on the first one of the plurality of functions.

In an embodiment, the operation of the second one of the plurality of functions is limited based, at least in part, on the first one of the plurality of function being in use.

In an embodiment, the operation of the second one of the plurality of functions is limited based, at least in part, on a level of use of the first one of the plurality of functions.

In an embodiment, the second one of the plurality of functions is limited further based, at least in part, on a power consumption level of system.

In an embodiment, the operation of the second one of the plurality of functions is limited by being disabled from use.

In an embodiment, the operation of the second one of the plurality of functions is limited, at least in part, by being transferred to a temporary storage location.

In an embodiment, the second one of the plurality of functions is associated with the host device and wherein the temporary storage location is located in the communication module.

In an embodiment, the second one of the plurality of functions is associated with the host device and wherein the temporary storage location is located in a location other than the host device and the communication module.

In an embodiment, the second one of the plurality of functions is at least partially restored to use and no longer limited upon a use of the first one of the plurality of functions being completed.

In an embodiment, the second one of the plurality of functions is at least partially restored to a level of operation at least partially dependent on operation of the first one of the plurality of functions.

In an embodiment, the second one of the plurality of functions is at least partially restored to a level of operation at least partially dependent on a level operation of the first one of the plurality of functions.

In an embodiment, a method is provided for interfacing with a medical device using a system, the system having a host device comprising a user interface configured to input and display information relating to the interfacing with the medical device, the system further comprising a communication module locally coupled to the host device and configured to communicate wirelessly with the medical device, the system, implemented by at least one of the host device and the communication module, having a security condition. The method comprises the steps of communicating with the system, using at least one of the host device and the communication module, with the medical device with a plurality of functions and disabling at least one of the plurality of functions, at least in part, from operating on the system based upon the security condition.

In an embodiment, the method further comprises the step of operating at least one of the plurality of functions on the system by running an application on at least one of the host device and the communication module. The disabling step disables the at least one of the plurality of functions by at least partially deleting the application.

In an embodiment, the disabling step disables the at least one of the plurality of functions by deleting the application.

In an embodiment, the communicating step runs the application to implement the at least one of the plurality of functions by running on the host device.

In an embodiment, the disabling step comprises disabling the application by removing the application from the host device.

In an embodiment, the disabling step disables the application by moving the application from the host device to the communication module.

In an embodiment, the disabling step comprises disabling at least one of the plurality of functions based upon the security condition is a communication function with the medical device.

In an embodiment, the method further comprises the step of restoring to the system the at least one of the plurality of functions deleted from the system only by a trusted source.

In an embodiment, a method is provided for interfacing with a medical device with a system, the system comprising a host device comprising a user interface configured to input and display information relating to the interfacing with the medical device, the system further comprising a communication module locally coupled to the host device and configured to communicate wirelessly with the medical device. The method comprises the steps of communicating with the system, implemented by the host device and the communication module, with the medical device with a function and ceasing the communicating step so that the function operates, at least in part, only for a predetermined duration.

In an embodiment, the method further comprises the step of extending the predetermined duration upon a user input.

In an embodiment, a method is provided for interfacing with a medical device with a system, the system comprising a host device comprising a user interface configured to input and display information relating to the interfacing with the medical device, the system further comprising a communication module locally coupled to the host device and configured to communicate wirelessly with the medical device, the system, implemented by at least one of the host device and the communication module, having a security condition, and a plurality of functions, wherein a first one of the plurality of functions is related to the interfacing with the medical device and a second one of the plurality of functions is not related with the interfacing with the medical device. The method comprises the steps of communicating with the medical device with the plurality of functions and limiting an operation of the second one of the plurality of functions based, at least in part, on the first one of the plurality of functions.

In an embodiment, the limiting step limits the operation of the second one of the plurality of functions based, at least in part, on the first one of the plurality of function being in use.

In an embodiment, the limiting step limits the operation of the second one of the plurality of functions based, at least in part, on a level of use of the first one of the plurality of functions.

In an embodiment, the limiting step limits the second one of the plurality of functions further based, at least in part, on a power consumption level of system.

In an embodiment, the limiting step limits the operation of the second one of the plurality of functions by being disabled from use.

In an embodiment, the limiting step limits, at least in part, the operation of the second one of the plurality of functions by being transferred to a temporary storage location.

In an embodiment, the second one of the plurality of functions is associated with the host device and wherein the limiting the temporary storage location is located in the communication module.

In an embodiment, the method further comprises the step of at least partially restoring to use and no longer limiting the second one of the plurality of functions upon a use of the first one of the plurality of functions being completed.

In an embodiment, the method further comprises the step of at least partially restoring to a level of operation the second one of the plurality of functions at least partially dependent on operation of the first one of the plurality of functions.

In an embodiment, the method further comprises the step of at least partially restoring to a level of operation the second one of the plurality of functions at least partially dependent on a level operation of the first one of the plurality of functions.

FIGURES

DESCRIPTION

The entire content of U.S. Provisional Application Ser. No. 61/427,390, filed Dec. 27, 2010 is hereby incorporated by reference.

Figure 1:
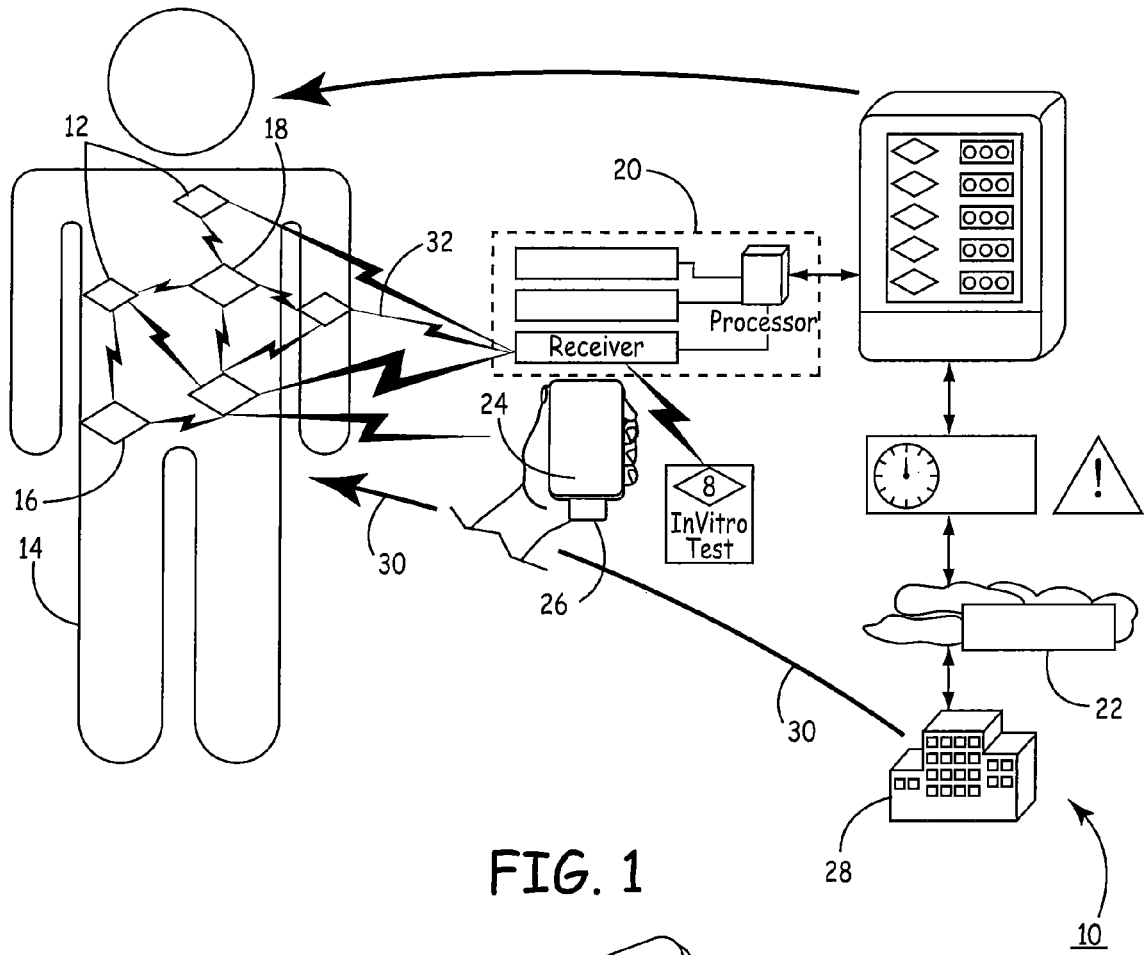
FIG. 1 is an illustration of a network to interface between implantable medical devices in a patient, including therapy delivery devices and sensors, and outside receptors utilizing a communications module coupled to a host device.

FIG. 1 is an illustration of an exemplary network 10 to interface between implantable medical devices 12 in patient 14, including therapy delivery devices 16 and sensors 18, and outside receptors 20. Information may flow from implantable medical devices 12 to external networks 22, while information and instructions may flow to implantable medical devices 12 from network 10. One device which may facilitate such information flows is the handheld consumer electronic device 24, or host, as depicted by a smartphone, for example, an iPhone™ smartphone[1] by Apple Inc. As illustrated, host 24 is operably, locally coupled to module 26 configured to facilitate communications and between and interfacing with implantable medical devices 12 and host 24. In various embodiments described below, host device 24 is locally coupled to communication module 26 either through a physical connector or by wireless communication. Alternative embodiments of host 24 are envisioned, including, but not limited to, products by Apple Inc. such as the iPod™ digital music player[2], iPad™ tablet computer[3] and MacBook™ computer[4], the BlackBerry™[5] smartphone by Research-in-Motion, Ltd., the Droid™ smartphone[6] and the Defy™ smartphone[7] by Motorola, Inc., the Optimus™ smartphone[8] by LG Electronics Inc., and the Evo™ smartphone[9] and Wildfire™ smartphone[10] by HTC Corp.

[1] iPhone is a trademark of Apple Inc.
[2] iPod is a trademark of Apple Inc.
[3] iPad is a trademark of Apple Inc.
[4] MacBook is a trademark of Apple Inc.
[5] BlackBerry is a trademark of Research-in-Motion, Ltd.
[6] Droid is a trademark of Motorola, Inc.
[7] Defy is a trademark of Motorola, Inc.
[8] Optimus is a trademark of LG Electronics Inc.
[9] Evo is a trademark of HTC Corp.
[10] Wildfire is a trademark of HTC Corp.

Advantageously, the use of an off-the-shelf, commercially available consumer electronic device may provide a common and easy to use standard user interface. Such host devices 24 may incorporate a proven and robust infrastructure for the writing and dissemination of applications in support of communications module 26. Host devices 24 may incorporate a family or platform of devices which may allow for single applications which may be useful on multiple devices. In addition, such commercial devices commonly incorporate common electronic connectors, both within device platforms and families and across device platforms and manufacturers. The commercial features of host devices 24 may further be utilized in support of medical applications, such as by providing easy accessibility to email, text and other forms of electronic communication. Additionally, existing medical applications may be utilized to supplement proprietary medical applications, providing, for instance, applications for regulating patient's 14 diet, weight, blood pressure, insulin, blood glucose levels and so forth.

As illustrated, host device 24 is locally coupled to communication module 26 by way of an electronic connector (obscured). The connector may be standard for host device 24 and may be utilized by host device 24 to interface with external data sources and power supplies. In various embodiments, communication module 26 may be configured to interface with multiple different types of host devices 24, e.g., by having multiple electronic connectors or by having a common connector (for example, a USB port, that can connect to differing devices). In various alternative embodiments, each communication module 26 is configured to function with only one particular type of host device 24.

Communication module 26 may be configured to communicate wirelessly with implantable medical devices 12 in patient 14. Host device 24 and module 26 together may be configured to perform various functions relating to interfacing with medical device 12, for instance, by receiving information from one or more of implantable medical devices 12 and, in some instances, provide the received information to host device 24. Module 26 may also be configured to receive information (e.g., data or instructions) from host device 24 for transmission to implantable medical devices 12 and transmit the received information to one or more of implantable medical devices 12. Host device 24 may be variably configured to display the information received from implantable medical devices 12 and/or to forward the information received from implantable medical devices 12 to other members of network 10, illustrated or not. Host 24 may be configured to transmit the information received by way of communications methods already incorporated into host device 24. For instance, where host device 24 is a smartphone, the host device may transmit the information over a cellular network, over a WiFi network or over a physical connection such as Ethernet or modem.

Host 24 and communication module 26 may together be further variably configured to allow a user to perform functions relating to interfacing with implantable medical device 12, such as by entering instructions for transmission to implantable medical devices 12 by way of module 26. In addition, host 24 may be configured to receive instructions from a third-party device by way of host device's 24 built-in communications systems. For instance, a medical professional operating at remote site 28 may be permitted to transmit instructions 30 to host device 24 by way of the cellular system, for instance, which may then be communicated to one or more of implantable medical devices 12 by way of communications module 26.

Figure 2:
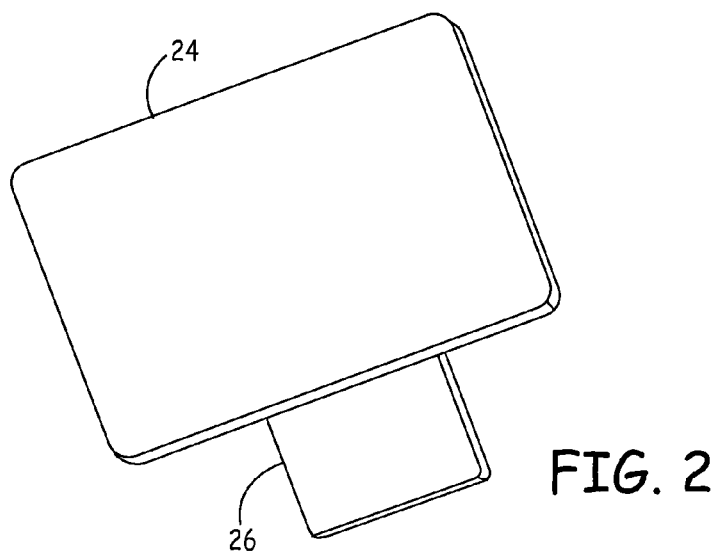
FIG. 2 is an exemplary embodiment of a communications module coupled to a host device.

FIG. 2 is an exemplary embodiment of communications module 26 coupled to host device 24, as illustrated a smartphone. Communications module 26 is configured with a connector which allows module 26 to be operatively connected to host device 24 according to the requirements and specifications of host device 24. As such, module 26 may be configured to be operatively connected to any similar model smartphone, in the illustrated example, interchangeably. In addition, any host device 24 with the same connection capability may be operatively connected to communications module 26.

In various embodiments, host device 24 may be configured with software, such as an application or "app" running on host device 24, to allow host device 24 to interface with communications module 26 according to the various functions described herein. Each application may correspond to one or more such function, for instance by providing a display for patient physiological data, data relating to the performance of medical device 12, and entering in programming parameters for transmittal to medical device 12, among other functions. The software may allow host device 24 to operate with module 26, display information received from implantable medical device 12 by way of module 26 and allow a user to input instructions to be transmitted to implantable medical device 12, among other functions. The software may be incorporated into module 26 and downloaded into host 24 when module 26 is plugged into host 24, or may be downloaded into host device 24 directly or remotely according to methods well known in the art.

In an embodiment, communications module 26 is configured to communicate 32 (FIG. 1) with implantable medical device 12 on the MICS/MEDS band. In one example, module 26 is approximately fifty (50) millimeters by fifty (50) millimeters and incorporates a thirty (30) pin connector. Communications module 26 incorporates one or more antennas as well as at least one processor to support communications.

Figure 3:
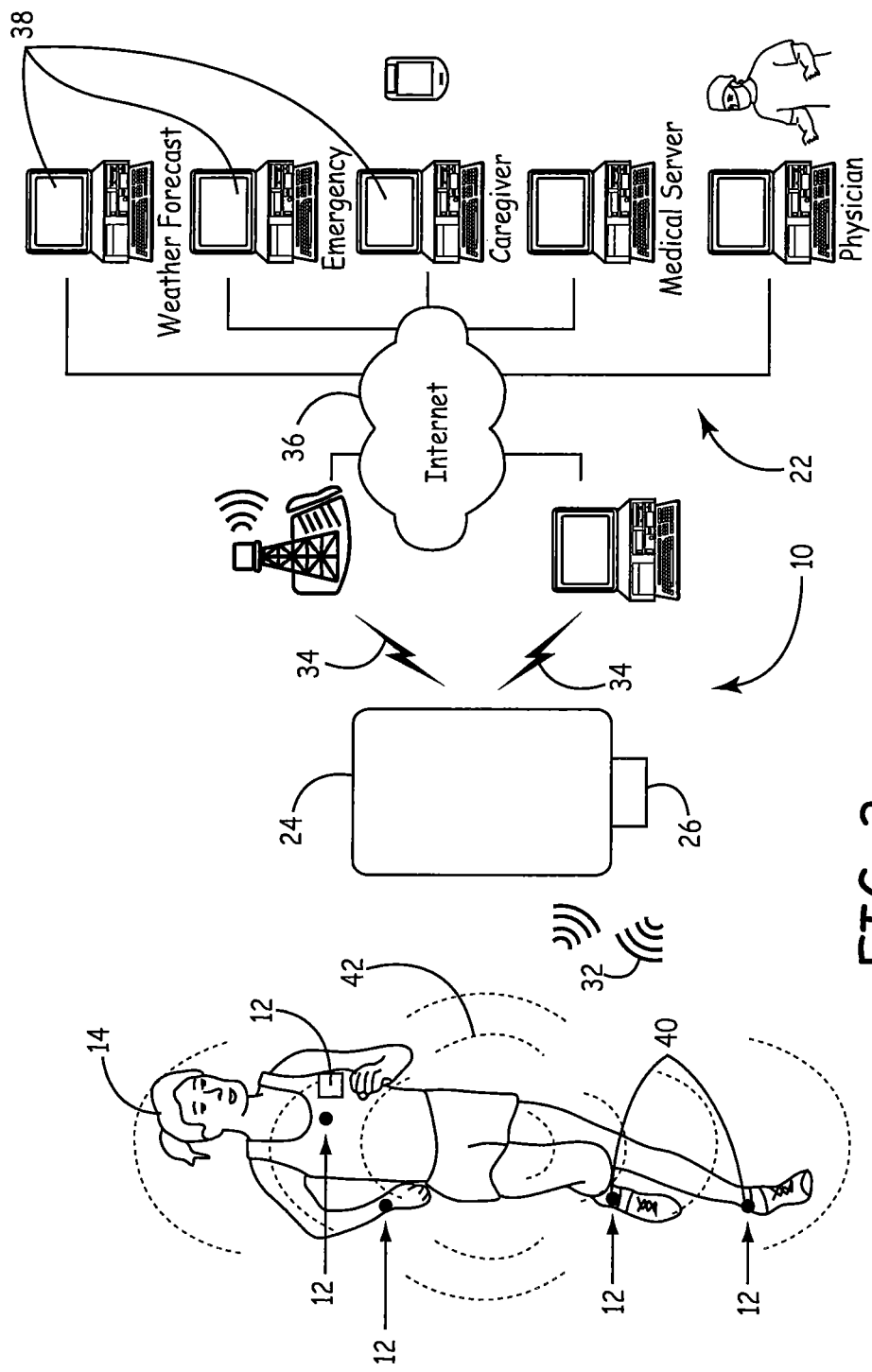
FIG. 3 illustrates an embodiment of a host device coupled to a module and configured to facilitate communications between an implantable medical device in a patient and a wider network.

FIG. 3 illustrates an embodiment of host device 24 coupled to module 26 and configured to facilitate communications 32 between implantable medical device 12 in the patient and a wider network 22. Communications module 26 permits communication between host device 24 and implantable medical device 12 of mobile patient 14. Host device 24 permits wireless communication 34 according to various standards with the Internet 36 and thus various third-party destinations 38.

In the illustrated embodiment, host device 24 and communications module 26 may be on the person of patient 14 and transmitting as patient 14 moves around. In various embodiments, communications module 26 may be separated from implantable medical device 12 by ten (10) meters or more. However, in certain embodiments, communications module 26 may not be configured to communicate with implantable medical device 12 at ranges longer than approximately ten (10) meters and may instead have a communication range of one (1) meter or less. By contrast, host device 24 may be configured to communicate on WiFi and/or cellular bands 34, for instance, at ranges conventionally from tens of meters to multiple kilometers.

In so doing, communications module 26, coupled with host device 24, may be configured to provide global connectivity for patients with implantable medical devices 12. In various embodiments, host devices 24 which are configured to communicate over communications systems available even in relatively remote places may deliver information from patients' 14 medical devices 12 to and receive instructions from medical providers in distant places 38. In such embodiments, host devices 24 may be devices which are already possessed by patient 14 or which may be acquired at relatively modest cost. Similarly, because communications module 26 may incorporate few features and functions other than to communicate with host device 24, communications module 26 may similarly be relatively inexpensive and useable in remote areas.

In addition, the use of host devices 24 such as commercially available, "off-the-shelf" devices detailed above, may provide for patient- and physician-centric applications to support maintenance of patient's 14 implantable medical device 12 and advance patient care. Patient 14 may be provided with details of their care on host device 24 in order for patient 14 to better understand their condition and what steps patient 14 may take outside of the strict function of their implantable medical device 12 to advance their treatment. Physicians may be provided on their own devices 38, either commercial devices or purpose-built devices, information similarly related to the status of patient 14 and implantable medical device 12, and may be provided with such information conveniently and without having to directly interface with patient 14. Thus, such information may be provided conveniently and at relatively low cost. In further instances, patient 14 and the physician may use the same host device 24 with different communications modules 26 attached or the same host device 24 using the same communications module 26 with additional functionality provided to the physician (e.g., by using a password).

In particular, patient-centric applications may include monitoring and reporting to patient 14 of adverse medical events and reactions to treatment, alerts instructing patient 14 to take a particular action, and physiologic information not necessarily related to their treatment. Physiologic information may include information such as blood pressure and weight. Additional patient-centric information may include educational materials for instructing patient 14 on living with various diseases and conditions, vital signs and instruction on activities such as eating, exercise and daily health logs. Additional patient-centric applications are envisioned.

In particular, physician-centric applications may include programming capabilities for implantable medical devices 12 of patient 14, providing patient 14 with medical advice and enabling various alternative forms of communication with patient 14 and other sources. Programming capabilities may include full programming capabilities for implantable medical devices 12. Alternatively, perhaps particularly for relatively complex devices which may cause a negative impact on patient 14 in the event of a patient reaction to a new therapy, full programming of implantable medical devices 12 may be curtailed for certain, relatively more complex devices. The sharing of health and wellness information may incorporate customized data viewing capabilities, for particular devices, patients 14 and physicians, as well as generalized health information and interfaces which may be presented on other, proprietary devices.

In addition to providing patient- and physician-centric applications, communications module 26 may provide such applications while allowing implantable medical devices 12 to become or maintain relatively small size and form factor, as well as to attain or maintain relatively low power consumption. By not needing to communicate over communication bands and according to communication standards which utilize relatively large antennas and consume relatively large amounts of power, such as those found on host devices 24 listed above, implantable medical devices 12 can use relatively short-range, low-power communications schemes such as those typically and historically utilized on implantable medical devices 12 while still maintaining the benefits of long-range communications. In so doing, the relatively small form factors and low power consumption of implantable medical devices 12 may be maintained.

It is to be recognized and understood that other sensors 40 may be utilized, including and without limitation, in an embodiment, one or motion sensors (e.g., a motion sensor positioned with respect to the body core and a motion sensor positioned with respect to an extremity), one or more tilt sensors (e.g., to assist in determining either a position of the body, an angle of repose of the body or both), and one or more oxygen sensors. Any and all of sensors 40 could communicate with host device 24 by way of communications module 26. Further, any and all of sensors 40 may also communicate with each other, or some of the other sensors 40, by way of, for example, a body area network 42 using, for example the MICS/MEDS band.

In an exemplary embodiment, body area network 42 may be utilized to communicate not only with any and all of sensors 40 but also may communicate with implantable medical device 12 or multiple implantable medical devices 12. Any and all of such implantable medical devices may communicate not only with each other and with any and all of such sensors 40 but also may communicate with host device 24 through communications module 26 using, for example the MICS/MEDS band.

Figure 4:
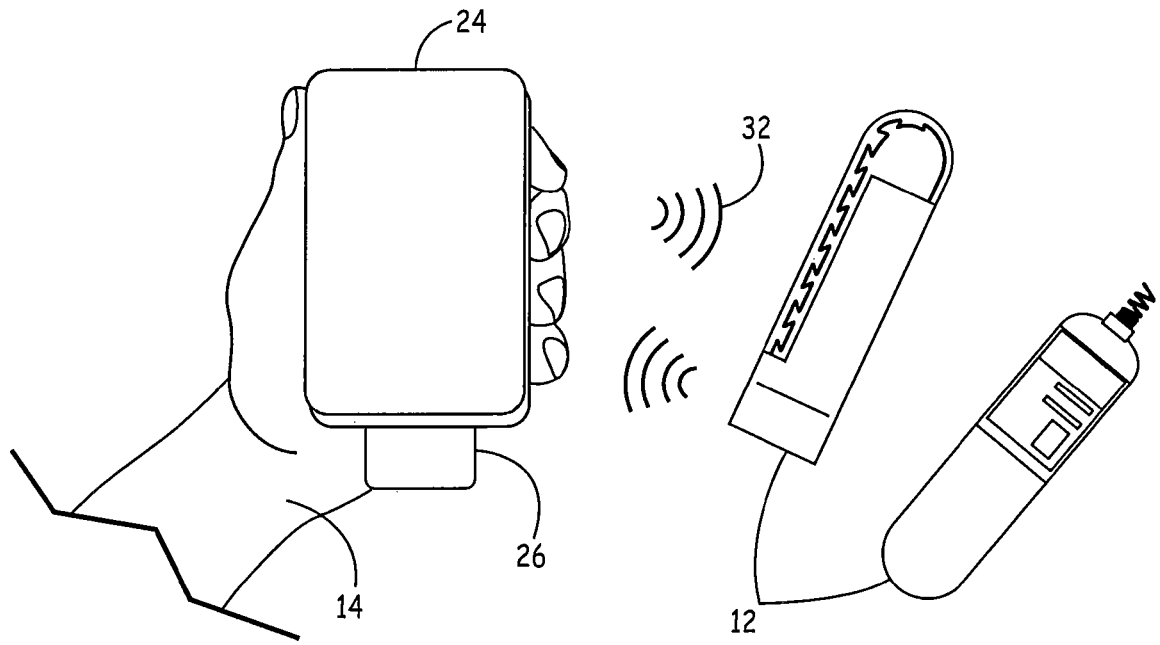
FIG. 4 is a depiction of a graphical application for a host device configured to facilitate interfacing with implantable medical devices.

FIG. 4 is an example depiction of a graphical application for host device 24 configured to facilitate interfacing with implantable medical devices 12. As depicted, the application provides data to patient 14 relating to the conduction of a basic exercise program or "basic workout". In such an embodiment, implantable medical device 12 may be related to providing a physiologic status of patient 14, such as blood pressure or heart rate. Because various host devices 24 incorporate different operating systems and different hardware, the various applications which are developed may be adapted for different host devices 24. For host devices 24, which incorporate a common operating system and the same or similar hardware, applications may be developed which are cross-functional.

Figure 5:
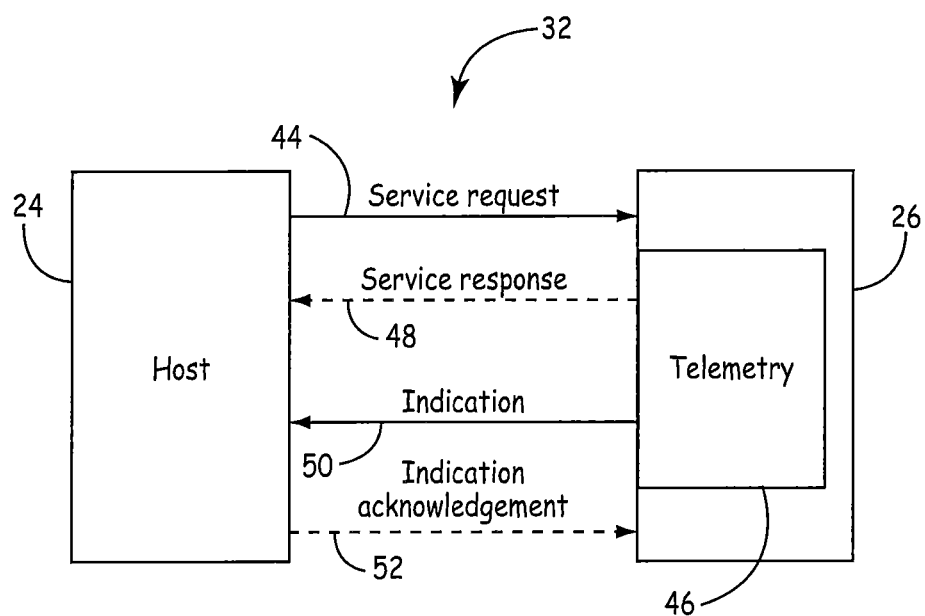
FIG. 5 is a diagram for conducting communications between the host device, the communication module and the implantable medical device.

FIG. 5 is a diagram illustrating an example series of communications 32 between host device 24, the communications module and implantable medical device 12. In particular, FIG. 5 illustrates example steps by which host device 24 initiates communication with implantable device 12 by making a service request 44 to telemetry module 46 of communications module 26 and receiving service response 48. Services which may be requested include, but are not necessarily limited to, a command to initialize, discover the presence of medical device 12, open communications, obtain data and close communications. FIG. 5 further illustrates the initiation of communication or, alternatively, the response to the service request by the communications module by transmitting indication signal 50. Such functions may be implemented in firmware on communications module 26 and may be acknowledged with indication acknowledgement 52.

Figure 6:
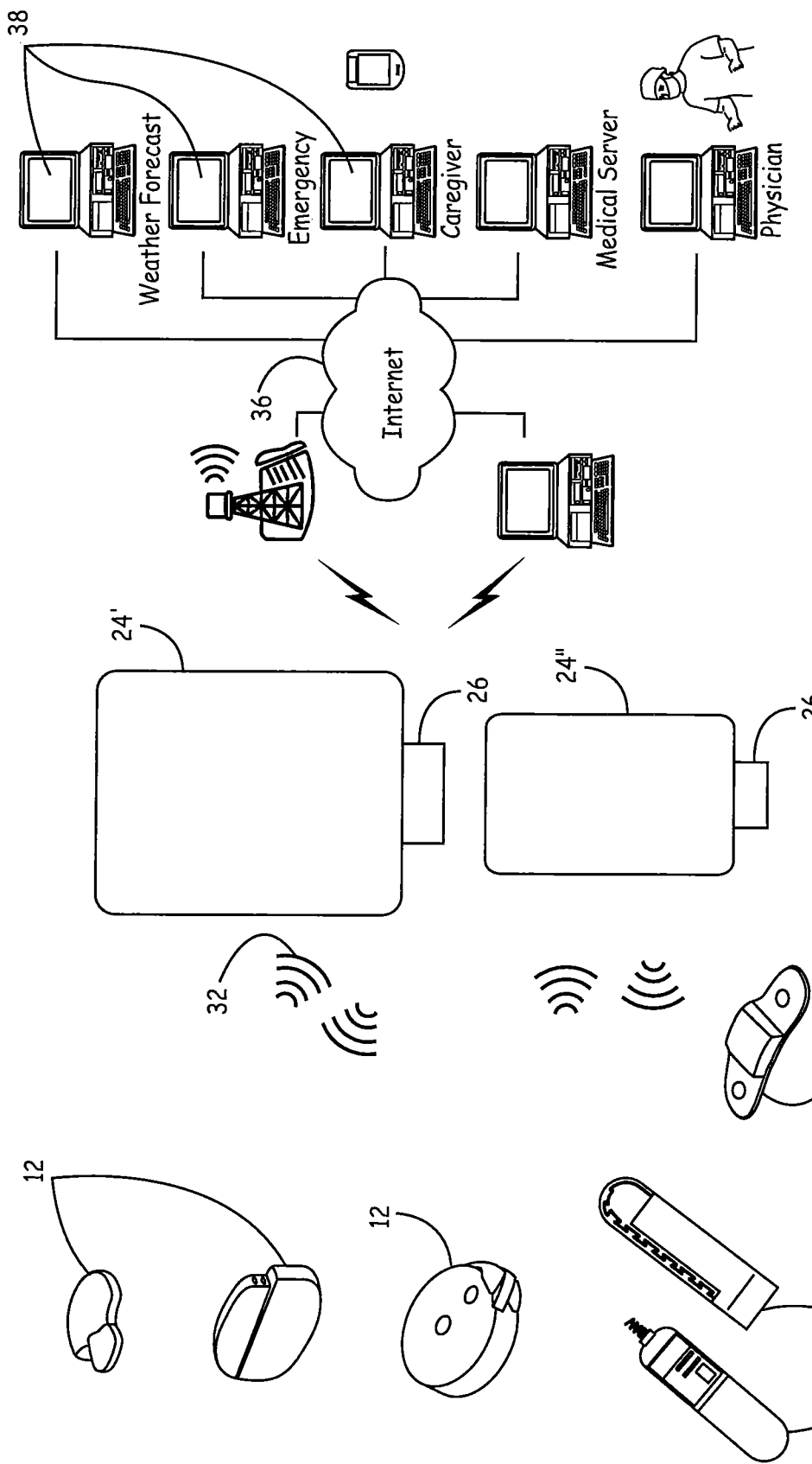
FIG. 6 is a depiction of utilizing multiple host devices of varying types to communicate with multiple medical devices and to facilitate communications between and among the multiple medical devices, the host devices and the third-party devices over the Internet.

FIG. 6 is a depiction of utilizing multiple host devices 24 of varying types to communicate 32 with multiple medical devices 12 and to facilitate communications between and among multiple medical devices 12, host devices 24 and the third-party devices 38 over the Internet 36. As illustrated, both a tablet computer host device 24' and a smartphone host device 24", in an embodiment an iPad™ tablet computer and an iPhone™ smartphone, respectively, are configured to communicate 32 with various medical devices 12, both implantable and non-implantable. The presence of multiple medical devices 12 and multiple host devices 24 need not interfere with the ability of various medical devices 12 and host devices 24 to communicate with one another.

Figure 7:
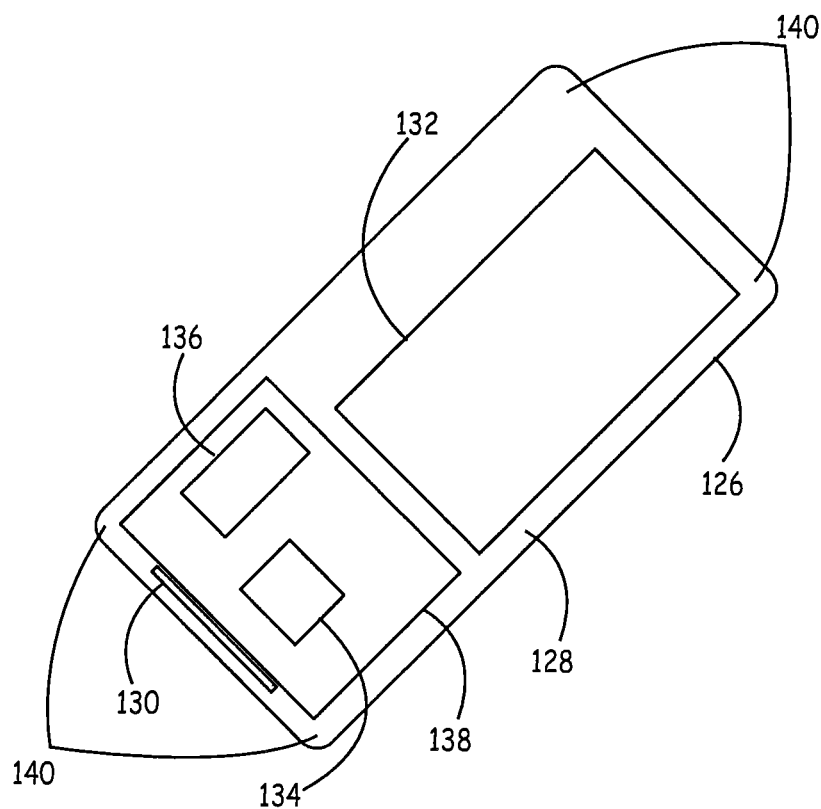
FIG. 7 is a depiction of an alternative embodiment of the communication module.

FIG. 7 is a depiction of an alternative embodiment of communications module 126. Rather than being a plug-in-style module 26 as shown, for instance, in FIG. 2, the communications module of FIG. 7 is incorporated in a casing or "skin" 128 to which host 24 device may be positioned, e.g., by "skin" 128 partially enveloping host device 24. As illustrated, casing 128 incorporates connector or data cord 130 to physically interface with host device 24. Electronics, including battery 132, processor 134, memory 136, motherboard 138 and antenna 140 are incorporated into the casing. Such components may be incorporated so as to be relatively flush with casing 128, thereby reducing the extent to which casing 128 increases the form factor of host device 24 relative, for instance, to the dongle implementation of communications module 26.

It is to be recognized and understood that, while the embodiments described above depict communication module 26, 126 configured to make a physical connection with host device 24, alternative embodiments of communication module 26 may be implemented. In particular, communication module 26 may be configured to operate without a physical connection to host device 24. In such embodiments, communication module 26 may have a power source such as battery 132 independent of host device 24 and may communicate with host device 24 according to various communication schemes detailed above with respect to communication between communication module 26 and medical device 12. Such communication schemes may include, but are not necessarily limited to, cellular, Bluetooth and WiFi. In such embodiments, host device 24 may be configured to maintain wireless communications with third party devices 38 according communication schemes described above, including, in various embodiments, the same scheme utilized for communications between communication module 26 and host device 24, without inhibiting communications between host device 24 and communication module 26 and the third party devices 38.

Providing patients 14 and physicians with relatively greater access to information and control of medical devices 12 may be beneficial in terms of the ability of patient 14 to understand and improve their own condition and the ability of a physician to treat patient 14. However, the proliferation of information and control may have side effects which may be mitigated. In particular, if a third party were to be able to access host device 24 with a coupled communication module 26, the third party may be able access personal and sensitive information about patient 14 and may, in certain circumstances, be able to impact the performance of patient's 14 device 12.

Applications ("apps") residing on or running on host device 24 and which perform various functions as described herein and including providing sensitive patient information or which allow for the modification of patient's 14 medical device 12 may be protected by a variety of security features, both known in the art, such as passwords and public-private keys, and proprietary features which are not widely known in the art. Such application-based security may be in addition to any validation or security provided generally to access to or operate host device 24 and/or in addition to any validation or access security based on a particular user of host device 24. However, a third party, given enough time and given the opportunity to make enough attempts, may find ways to break the security features of medical device 12 applications. In an embodiment, a user may be given only a limited number of attempts to pass the various security features.

As a consequence of a failure to pass the security features in the requisite number of attempts or, perhaps, any other reason application security fails, such as by biometric failure, various contingency actions may occur to ensure the security of patient's 14 information and the integrity of patient's 14 medical device 12. In an embodiment, at least some or, perhaps all applications relating to patient's 14 medical device 12 may be disabled. Such disabling could be permanent, could be for a predetermined duration or period of time to allow for host device 24 to be recovered, could be until other, perhaps more basic, security measures could be achieved, such as basic host device 24 access, or could be until a medical application authorization is delivered to host device 24, either locally or remotely. Alternatively, such one or more medical application may be deleted from host device 24, perhaps rendering host device 24 inoperable to communicate with medical device 12, either by rendering host device 24 inoperable to interface with communication module 26 altogether or by rendering communication module 26 inoperable to communicate with medical device 12 while maintaining the connection between host 24 and module 26.

In such an embodiment, host 24 may need to be re-loaded with application software in order to be useful for interfacing with medical device 12. In such a circumstance, the loading of application software may be performed under the supervision or with the acquiescence of a trusted provider, such as patient's physician or a trusted representative of the physician.

In an embodiment, the application software may be "locked" and access denied without intervention by a trusted source. In such an embodiment, the application may not be deleted altogether. However, access may be denied until the application is "unlocked". In embodiments where the application is deleted altogether and in embodiments where the application is merely "locked", the user may have not more than three total attempts to pass the security features before the contingency event occurs. In alternative embodiments, variably more or fewer unsuccessful attempts may be made.

In additional embodiments, various medical device software applications are incorporated into host device 24 which are desired for the user to be able to access the functions associated with the application for a only a predetermined duration. For instance, patient 14 may be advantageously provided with an application which mimics the function of a Holter monitor. In such an embodiment, patient's 14 physician may desire to have Holter monitor data for a standard time period, for instance three days. In the interest both of not consuming excessive amounts of memory capacity on patient's 14 host device 24, and to prevent excessive information being available in the event the information is compromised, the Holter software application may be included with a function to automatically delete itself after a predetermined duration of operation of the Holter function, for instance the three days over which information is desirably gathered. In such embodiments, the duration of operation may begin upon a first operation of the Holter function. Advantageously, the Holter monitor information may thus be gathered without creating a long term source of information which may become compromised or by creating a long term and otherwise unneeded use of memory space on host device 24 or communication module 26.

Similarly, a medical application residing on or running on host device 24 may be prescribed by an authorized medical person for use by patient 14 or by a caregiver for patient 14 for a specific use and/or for a specific predetermined duration. In this embodiment, the application may be provided with the prescription limitations either at the time of loading or installing the application either on host device 24 or on another device from which host device 24 runs the application or at some earlier or later time, perhaps when the user logs on or when the application is first accessed or accessed for a particular number of uses or for an amount of use when the prescription information may be accessed from a remote site or downloaded to the device.

As an example, once the application has performed a particular number of operations or performed a level of treatment, the application may retrieve application prescription information or retrieve updated or replacement prescription information. The prescription information may limit the usefulness and/or operation of the application in some way as prescribed. The limit may be a time period of use as described in relation to the Holter monitor example. Or the limit on predetermined duration may be on a duration of elapsed time, on a number of uses, an amount or degree of care, or an amount or degree of information.

Various conditions may be combined to account for the predetermined duration, including but not limited to combining duration of operation and duration of elapsed time; number of operations and duration of elapsed time; number of operation and a duration of operation; and a number of operations, a duration of operation and a duration of elapsed time. Upon or following the fulfillment of the prescription, the application may retrieve a new prescription, for example a prescription refill by an authorized authority, the application may be disabled, operation of the application may be restricted or the application may be deleted.

In an embodiment, an application may seek authorization from an appropriate authority at each operation or at a number of operations or a level of treatment, thereby providing the predetermined duration being extendable upon a user input. Thus, instead of being loaded or pre-loaded with prescription information, the application, through host device 24, may seek authorization on an ongoing basis from an authorized authority. For example, a remote database may be accessed containing such prescription information. The remote prescription database then could be under the control of the authorized authority and an up-to-date knowledge of the current state of all prescriptions could be maintained. Failure to obtain authorization could result in any or all of the scenarios described above with respect to expiration or failure of the prescription.

A further complication to the effective use of the software applications may be raised by the potential for various applications on host device 24 to interfere with the operations of the software application related to interfacing with medical devices 12. In certain circumstances, an application not related with interfacing with medical devices 12 on host device 24 may seek to commence operation. Doing so may, at minimum, consume processing and memory resources of host device 24 which may be needed by a medical device application relating to interfacing with medical devices 12. In certain embodiments in which host device 24 is configured to run only one software application at a time, the activation of a second software application may preempt and disable the medical device software application. Such an event may interrupt important interaction with medical device 12. Further, the operation of another application by host device 24 may cause a known or unknown conflict with the operation of the medical device application either resulting in less than optimum performance by the medical device application, by the conflicting application or both.

In an embodiment, the medical application having a first function interfacing with medical devices 12 may preemptively disable at least one other software application having a second function not interfacing with medical devices 12 on host device 24 while the medical device software application is operating. In an embodiment, the medical application preemptively disables all other software applications on host device 24 while the medical application is in use. In such embodiments, the second function is at least partially restored to use or no longer limited upon the use of the first function related to interfacing with medical devices 12 being completed. In various embodiments, restoration of the second function is at least partially dependent on the operation or lack thereof of the first function. In such embodiments, when the first function is utilized in a reduced operation mode, such as a standby mode or a monitoring mode, the second function may be partially restored to operation.

In an embodiment, a level of use of the first function of the medical application may provide a basis for the operation of the second function being limited. In an embodiment, a total power consumption of host device and communication device may be provide a basis for the operation of the second function being limited. In such an embodiment, when system power consumption approaches a predetermined maximum, functions not related with interfacing with medical devices 12 are curtailed while functions related to interfacing with medical devices 12 are maintained.

In various embodiments of host devices 24, the medical application may utilize various features of host device 24 operating system to prevent other applications from operating. In such circumstances, the medical application may be utilized and operated in the knowledge that an extraneous software applications having functions not related to interfacing with medical devices 12 will be disabled from use and not consume system resources or preempt entirely the operation of the medical device software application or otherwise conflict with the operation of the medical application. Alternatively, another application having a second function may be allowed to start and/or be run by host device 24 but the level of use or extent of operation of the other application may be limited. For example, a background application could still run, for example, to alert the user of a calendar alarm, an incoming voicemail or text. It could be that such an operation would cause other applications being run or to be run by host device 24 to be wholly or partially quarantined until the medical application deems it appropriate to release the quarantine, for example, when the medical application is finished or during certain operations or portions of operation of the medical application.

Figure 8:
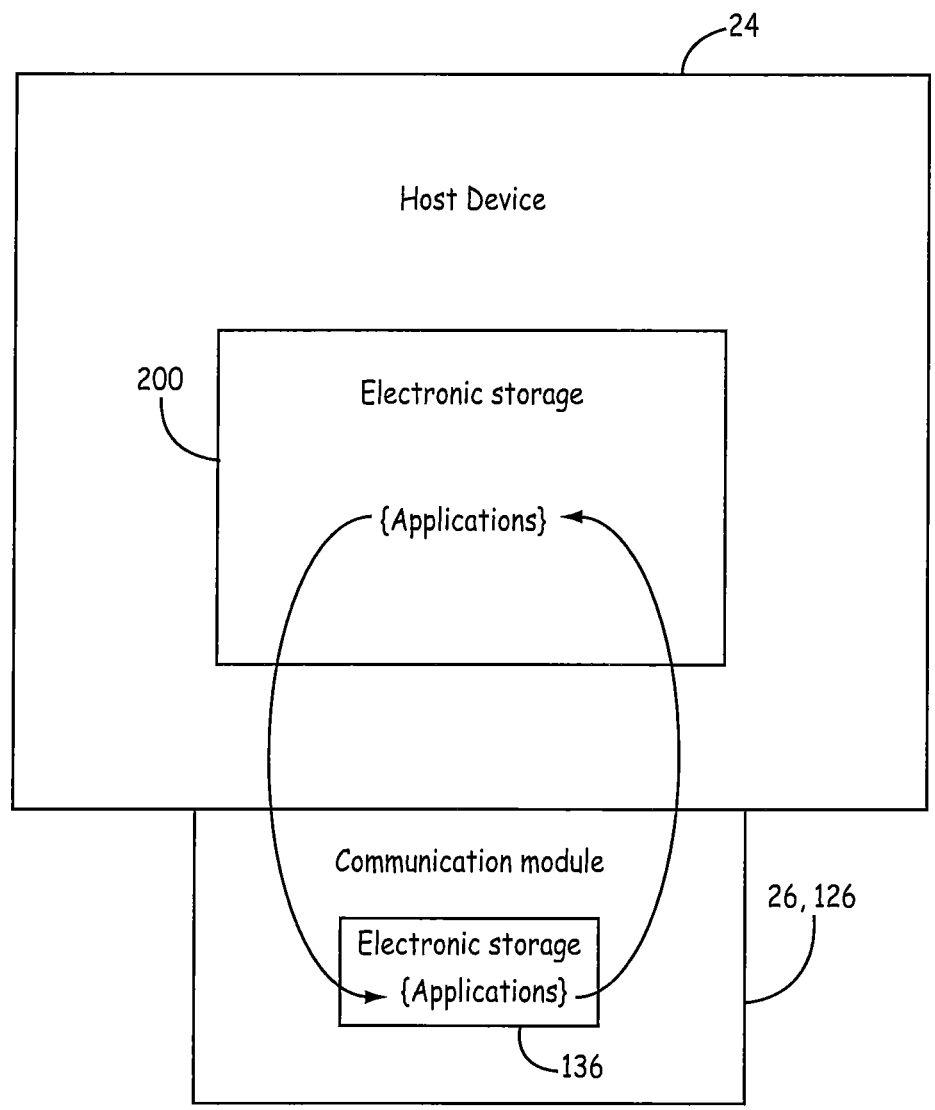
FIG. 8 is a block-level diagram of shifting applications between the host device and the communication module.

Alternatively, and in certain embodiments to further mitigate the likelihood of a secondary software application from starting up and consuming system resources or preempting the operation of the medical device software application or otherwise conflicting with the operation of the medical application, at least one software application, already existing on host device 24, may be copied from host device 24 to a temporary storage location in memory module 136 on communication module 26, 126 or elsewhere and then deleted from the electronic storage 200 of host device 24, or simply moved from host device 24 to another memory location not in either host device 24 or communication module 26 for temporary safekeeping. Such embodiments are illustrated in FIG. 8. In an embodiment, all software applications on host device 24, other than the medical device software application, are moved or copied in this manner. In this way, the other application or all other applications running on host device 24 or to be run on host device 24 are prevented from running since, simply, such application or applications have been removed, albeit temporarily, from host device 24. Thus, conflict or interference may be prevented between the medical application and the other potentially conflicting or interfering application or applications. Upon completion of the operation of the medical device application or upon the completion of a degree of operation of the medical application or during a certain period of operation of the medical application, the various software application or applications that were transferred to communication module 26, 126 or elsewhere may be transferred back to host device 24 and again become operational as before.

It is recognized and understood that host device 24 may also be under power and current constraints. Host devices 24 may incorporate multiple wireless communication schemes which may consume relatively more or less power in relation to the other communication schemes. One or more other applications, other than the medical application associated with the communications module, may also be run on host device 24 which may affect the amount of power being consumed by host device 24.

Still further, any connector 130 through which communications module 26, 126 may physically connect to host device 24 may have certain current and/or power limitations imposed by the manufacturer, provider, user or operator of host device 24. Communications module 26, plugging into host device 24 through such connector 130 may be mindful of those limitations so as not to impair or risk impairing operation of the host device itself. Communications module 26 may have various communications schemes from which to select, for example, Bluetooth, WiFi, inductive telemetry and MICS/MEDS, which may take varying amounts of power and may provide various functions, for example, programming, telemetry, etc., which also may take varying amounts of power. Thus, it may be impractical to design communications module 26 which, under all circumstances in any configuration and performing any permissible tasks, would not exceed the limit on power available through connector 130 with host device 24. Alternatively stated, if all features and all configurations had to be accommodated at any time, then the feature set and configuration be limited in order to ensure that the power limitation of host device 24 is not exceeded.

In an embodiment, the medical application having a first function configured to interface with medical devices 12 being run by host device 24, either locally or remotely, or a separate or ancillary application to the medical application, may monitor the power being consumed by communications module 26 and/or may monitor the current being drawn from host device 24 through connector 130. When the current/power limit is reached or approached or when some other current/power threshold is reached, then the monitoring function of an application could either limit the operation of the medical application, perhaps by limiting the features, functions or configuration of communications module 26 in order to stay at or below the current/power threshold and/or limit. In an embodiment, the medical application would, at least temporarily, cease operation, or resort to skeletal operation, either for a period of time or until the features, operation or configuration could be restored without exceeding the current/power threshold/limit.

Figure 9:
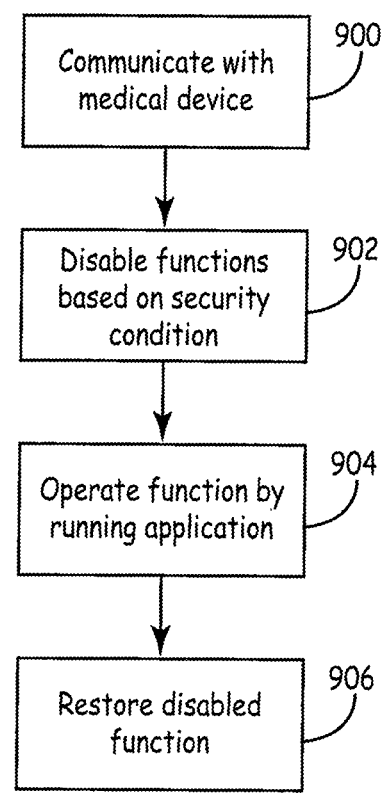
FIG. 9 is a flowchart for interfacing with a medical device by disabling one of a plurality of functions based on a security condition.

FIG. 9 is a flowchart for interfacing with a medical device by disabling one of a plurality of functions based on a security condition. At least one of host device 24 and communication device 26 communicates (900) with medical device 12 using a plurality of functions. At least one of the plurality of functions is disabled (902) based upon a security condition, as described in detail above. At least one of the plurality of functions is operated (904) on at least one of host device 24 and communication device 26 by running an application on at least one of host device 24 and communication device 26. In such an embodiment, the disabling step (902) disables at least one of the plurality of functions by at least partially deleting the associated application. In various embodiments, the at least one of the plurality of functions is restored (906) to at least one of host device 24 and communication device 26. In such embodiments, the restoration may occur only upon an action by a trusted source, such as a medical professional.

Figure 10:
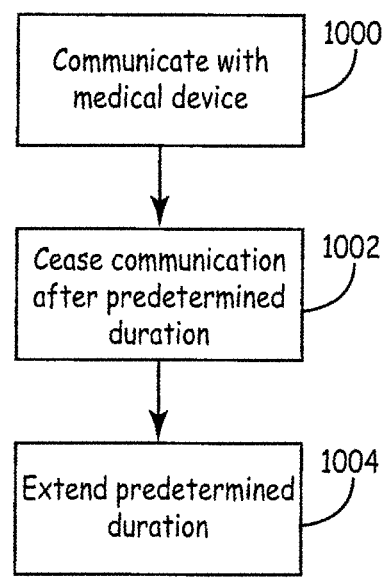
FIG. 10 is a flowchart for interfacing with a medical device by providing a function that operates for only a predetermined duration.

FIG. 10 is a flowchart for interfacing with a medical device by providing a function that operates for only a predetermined duration. At least one of host device 24 and communication device 26 communicates (1000) with medical device 12 using a function. The communication step (1000) ceases (1002) so that the function operates only for a predetermined duration. The ceasing communication step (1002) may be based on various criteria as described above, including, but not limited to a duration of operation, a duration of elapsed time, a number of operations, and combinations of factors thereof. In various embodiments, the predetermined duration may be extended (1004) upon a user input. In an embodiment, the user is a trusted source, such as a medical professional.

Figure 11:
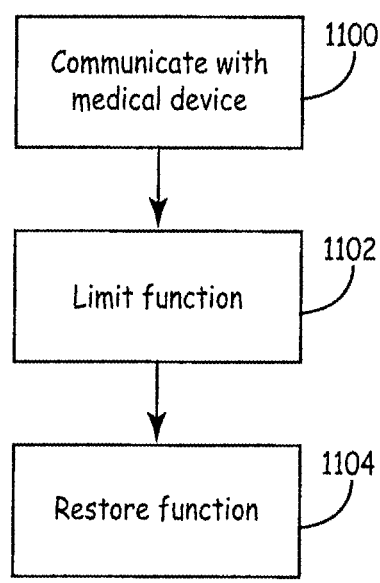
FIG. 11 is a flowchart for interfacing with a medical device by limiting an operation of a second function based on an operation of a first function.

FIG. 11 is a flowchart for interfacing with a medical device by limiting an operation of a second function based on an operation of a first function. At least one of host device 24 and communication device 26 communicates (1100) with medical device 12 using at least a first one of a plurality of functions. An operation of a second one of the plurality of functions is limited (1102) based on the first one of the plurality of functions. The limiting step (1102) may be based on various factors, including use of the first function, level of use of the first function and power consumption level, as detailed above. Limitation of the second function may include disabling the second function from use and transferring the second function to a temporary storage location, variably located on communication module 26 or elsewhere other than host device 24 and communication module 26. The second function may be restored (1104) upon a use of the first function being completed or otherwise based on a level of use of the first function.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for interfacing with a medical device, comprising:
   a host device comprising a user interface configured to receive input and display information relating to the interfacing with the medical device; and
   a communication module locally coupled to the host device and configured to communicate wirelessly with the medical device;
   wherein at least one of the host device and the communication module are configured to store an application for interfacing with the medical device, and at least one of the host device and the communication module are configured to execute the stored application that, when executed, enables the system, implemented by the host device and the communication module, to interface with the medical device;
   wherein the system, implemented by at least one of the host device and the communication module, has a security condition;
   wherein at least one of the host device and the communication module modify the application in response to the security condition; and
   wherein at least one of the host device and the communication module modify the application by moving the application from the host device to the communication module.

2. The system of claim 1 wherein the host device stores and executes the application for interfacing with the medical device.

3. A system for interfacing with a medical device, comprising:
   a host device comprising a user interface configured to receive input and display information relating to the interfacing with the medical device; and
   a communication module locally coupled to the host device and configured to communicate wirelessly with the medical device;
   wherein at least one of the host device and the communication module are configured to store an application for interfacing with the medical device, and at least one of the host device and the communication module are configured to execute the stored application that, when executed, enables the system, implemented by the host device and the communication module, to interface with the medical device;
   wherein the system is configured to operate the application for only a predetermined duration;
   wherein the predetermined duration is based on a duration of operation of one or more functions of the application.

4. The system of claim 3 wherein the predetermined duration is based on a duration of elapsed time.

5. A system for interfacing with a medical device, comprising:
   a host device comprising a user interface configured to receive input and display information relating to the interfacing with the medical device; and
   a communication module locally coupled to the host device and configured to communicate wirelessly with the medical device;
   wherein at least one of the host device and the communication module are configured to store an application for interfacing with the medical device, and at least one of the host device and the communication module are configured to execute the stored application that, when executed, enables the system, implemented by the host device and the communication module, to interface with the medical device;
   wherein the system is configured to operate the application for only a predetermined duration; and
   wherein the application is characterized by a number of operations and wherein the predetermined duration is based on the number of operations.

6. The system of claim 5 wherein the predetermined duration is based on a combination of the number of operations and a duration of elapsed time.

7. A system for interfacing with a medical device, comprising:
   a host device comprising a user interface configured to receive input and display information relating to the interfacing with the medical device; and
   a communication module locally coupled to the host device and configured to communicate wirelessly with the medical device;
   wherein at least one of the host device and the communication module are configured to store a first application for interfacing with the medical device, and at least one of the host device and the communication module are configured to execute the stored first application that, when executed, enables the system, implemented by the host device and the communication module, to interface with the medical device;
   wherein the host device is configured to store and execute a second application that is not related with the interfacing with the medical device, wherein at least one of the host device or the communication module limits operation of the second application by the first application, wherein the operation of the second application is limited by being transferred to a temporary storage location.

8. The system of claim 7 wherein the operation of the second application is limited by the first application being in use.

9. The system of claim 7 wherein the second application is limited by being transferred to a temporary storage location of the communication module.

10. The system of claim 7 wherein the second application is transferred back from the temporary storage location at least partially dependent on operation of the first application.

11. The system of claim 10, wherein the second application is transferred back from the temporary storage location when the first application is no longer in use.

12. A method for interfacing with a medical device using a system comprising a host device comprising a user interface configured to receive input and display information relating to the interfacing with the medical device, and a communication module locally coupled to the host device and configured to communicate wirelessly with the medical device, wherein at least one of the host device and the communication module are configured to store an application for interfacing with the medical device, and at least one of the host device and the communication module are configured to execute the stored application that, when executed, enables the system, implemented by the host device and the communication module, to interface with the medical device, the method comprising:

detecting a security condition of the system implemented by at least one of the host device and the communication module; and modifying the application in response to the security condition;

wherein the host device stores and executes the application, and wherein modifying the application comprises moving the application from the host device to the communication module.

13. A method for interfacing with a medical device with a system, the system comprising a host device comprising a user interface configured to receive input and display information relating to the interfacing with the medical device, and a communication module locally coupled to the host device and configured to communicate wirelessly with the medical device, wherein at least one of the host device and the communication module are configured to store an application for interfacing with the medical device, and at least one of the host device and the communication module are configured to execute the stored application that, when executed, enables the system, implemented by the host device and the communication module, to interface with the medical device, the method comprising:

operating the application by at least one of the host device and communication module to interface with the medical device; and disabling the application from operating on the at least one of the host device and the communication module after a predetermined duration;

wherein the application is characterized by a number of operations and wherein the predetermined duration is based on the number of operations.

14. The method of claim 13 wherein the predetermined duration is based on a combination of the number of operations and a duration of elapsed time.

15. A method for interfacing with a medical device with a system comprising a host device comprising a user interface configured to receive input and display information relating to the interfacing with the medical device, and a communication module locally coupled to the host device and configured to communicate wirelessly with the medical device, wherein at least one of the host device and the communication module are configured to store a first application for interfacing with the medical device, and at least one of the host device and the communication module are configured to execute the stored first application that, when executed, enables the system, implemented by the host device and the communication module, to interface with the medical device, and wherein the host device is configured to store and execute a second application that is not related with the interfacing with the medical device, the method comprising: limiting an operation of the second non-interfacing application by the first interfacing application, wherein limiting the operation of the second non-interfacing application includes transferring the second non-interfacing application to a temporary storage location.

16. The method of claim 15, wherein limiting the operation of the second non-interfacing application comprises limiting the second application based on a level of use of the first interfacing application.

17. The method of claim 15 wherein transferring the second application to a temporary storage location comprises transferring the second application to a temporary storage location of the communication module.

18. The method of claim 15, further comprising transferring the second application back from the temporary storage when the first application is no longer in use.

19. A system for interfacing with a medical device, comprising:

a host device comprising a user interface configured to receive input and display information relating to the interfacing with the medical device; and a communication module locally coupled to the host device and configured to communicate wirelessly with the medical device;

wherein at least one of the host device and the communication module are configured to store an application for interfacing with the medical device, and at least one of the host device and the communication module are configured to execute the stored application that, when executed, enables the system, implemented by the host device and the communication module, to interface with the medical device;

wherein the system, implemented by at least one of the host device and the communication module, has a security condition;

wherein at least one of the host device and the communication module modify the application in response to the security condition; and wherein at least one of the host device and the communication module:

receives input from a trusted provider subsequent to modifying the application; and restores the application in response to the input from the trusted provider.

20. A method for interfacing with a medical device using a system comprising a host device comprising a user interface configured to receive input and display information relating to the interfacing with the medical device, and a communication module locally coupled to the host device and configured to communicate wirelessly with the medical device, wherein at least one of the host device and the communication module are configured to store an application for interfacing with the medical device, and at least one of the host device and the communication module are configured to execute the stored application that, when executed, enables the system, implemented by the host device and the communication module, to interface with the medical device, the method comprising:

detecting a security condition of the system implemented by at least one of the host device and the communication module;

modifying the application in response to the security condition;

receiving input from a trusted provider subsequent to modifying the application; and restoring the application in response to the input from the trusted provider.

* * * * *